United States Patent [19]

Bur et al.

[11] Patent Number: 5,384,079
[45] Date of Patent: Jan. 24, 1995

[54] METHOD FOR DETECTING THERMODYNAMIC PHASE TRANSITIONS DURING POLYMER INJECTION MOLDING

[75] Inventors: Anthony J. Bur, Rockville; Francis W. Wang, Gaithersburg, both of Md.; Charles L. Thomas, Philadelphia; Joseph L. Rose, State College, both of Pa.

[73] Assignee: The United States of America as represented by the Secretary of Commerce, Washington, D.C.

[21] Appl. No.: 1,728

[22] Filed: Jan. 6, 1993

[51] Int. Cl.6 .............................................. B29C 45/76
[52] U.S. Cl. .................................. 264/21; 250/459.1; 264/22; 264/40.2; 264/328.18
[58] Field of Search ............... 264/22, 25, 40.2, 328.1, 264/328.18, 21; 250/573, 574, 458.1, 459.1

[56] References Cited

U.S. PATENT DOCUMENTS

| | | |
|---|---|---|
| 3,659,974 | 5/1972 | Neugroschl . |
| 4,529,306 | 7/1985 | Kilham et al. . |
| 4,651,011 | 3/1987 | Ors et al. . |
| 4,672,218 | 7/1987 | Chrisman et al. . |
| 4,798,954 | 1/1989 | Stevenson . |
| 4,827,121 | 5/1989 | Vidrine, Jr. et al. . |
| 4,904,080 | 2/1990 | Afromowitz . |
| 5,009,102 | 4/1991 | Afromowitz . |
| 5,037,763 | 8/1991 | Petisce . |
| 5,063,297 | 11/1991 | Hardenbrook et al. . |

Primary Examiner—Mathieu D. Vargot
Attorney, Agent, or Firm—Larson & Taylor

[57] ABSTRACT

A method is provided for measuring the onset of polymer solidification, i.e. phase transitions from liquid to crystal or liquid to glass, during injection molding to detect characteristic fluorescence radiation from a dye which has been doped into the polymer at very low concentration. The method involves the use of a calibration relationship between the fluorescence intensity and temperature of the doped polymer in order to determine distinct features which characterize the onset of solidification.

11 Claims, 9 Drawing Sheets

METHOD FOR DETECTING THERMODYNAMIC PHASE TRANSITIONS DURING POLYMER INJECTION MOLDING

FIELD OF THE INVENTION

The present invention relates to the injection molding of polymers and, more particularly, to a method for enabling the detection of thermodynamic phase transitions in a polymer during injection molding.

BACKGROUND OF THE INVENTION

It is well known in the art to use fluorescent dyes in dopant concentrations to monitor changes in certain specified characteristics of a given material. In particular, dyes have been used to probe molecular dynamics by chemically tagging them to a host molecule, to measure molecular orientation, to measure diffusion constants, to monitor polymerization, and to monitor the degree of cure of a curing thermoset material. In each of these applications, the fluorescent dye is chosen in accordance with the relationship between its spectral characteristics and the material property being examined.

For example, molecular rotor dyes such as 1-(4-dimethylaminophenyl)-6-phenyl-1,3,5 hexatriene (DMA-DPH):

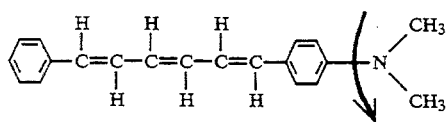

have been used to monitor the cure of thermoset materials, and to monitor polymerization. These dyes display fluorescence spectra whose intensity is dependent on the viscosity in the molecular neighborhood of the dye. Upon absorbing excitation energy, a molecular rotor can decay to its ground state via fluorescence radiation or by radiationless decay, i.e. energy transferred to molecular vibrations or rotations. For DMA-DPH, the amount of radiationless decay is regulated by rotations about the chemical bond at the end group as depicted by the arrow. This intramolecular rotational motion creates potential radiationless decay paths if its relaxation time, $\tau_r$, is shorter than or approximately equal to the fluorescence decay time $\tau_f$ of the dye, usually tens of nanoseconds. For $\tau_r \gg \tau_f$, maximum fluorescence radiation and minimum radiationless decay is observed.

Other types of dyes which may be used to analyze changes in various material properties are those which emit both monomer and excimer fluorescence. The radiated fluorescence energy is distributed between monomer and excimer modes of decay in accordance with the viscosity of the neighborhood. An example of this type of dye is bis(pyrene) propane (BPP) which contains two fluorescent pyrene molecules joined by a flexible propane linkage as shown below:

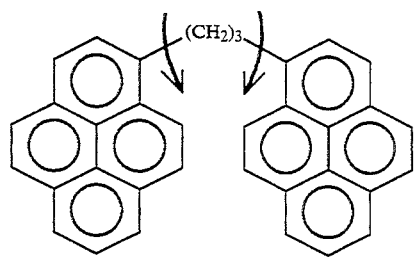

When one pyrene molecule absorbs excitation energy at 340 nm, two paths of fluorescence decay are possible. The first is by monomer decay at 380 and 400 nm; that is, the pyrene molecule displays its characteristic fluorescence without interaction with the other pyrene. The second is an excimer decay in the range of 450 to 550 nm which occurs when the excited pyrene forms an excimer with its unexcited pyrene neighbor by rotating to a position of close molecular contact. The probability that the excited pyrene can move into the proper position to form an excimer before its own decay occurs is dependent on $\tau_r$, the intramolecular rotational relaxation time of the dye, which is proportional to the ratio $\eta/T$ where $\eta$ is a microscopic or molecular viscosity in the neighborhood of the dye and T is the temperature. Thus, for excimer producing dyes as well as for molecular rotors, rotational relaxation time plays a prominent role in the production of fluorescence radiation.

U.S. Pat. No. 5,037,763 to Petisce and U.S. Pat. No. 4,651,011 to Ors disclose methods of using fluorescent dye molecules incorporated into a curing material to measure the increase in viscosity which arises during a chemical change accompanying epoxy curing or polymerization. However, these methods require background corrections, absolute intensity measurements or uniform mixing of dye and resin. Moreover, these methods do not consider viscosity changes which occur during an accompanying phase transition in a chemically stable polymer, and they do not consider measurement of free volume cell size, heat of crystallization or crystallinity.

SUMMARY OF THE INVENTION

The present invention discloses a method of detecting thermodynamic phase transitions in a polymer during injection molding comprising the steps of:
  mixing a fluorescent dye with a polymer;
  injecting said fluorescent dye and polymer into a mold;
  exciting said fluorescent dye with a light source;
  adjusting temperature of said polymer to effect a phase transition in said polymer;
  detecting changes in fluorescence intensity at various time intervals in said fluorescent dye during said step of adjusting;
  developing a fluorescence intensity profile by plotting said changes in fluorescence intensity versus time; and
  determining phase transitions in said polymer from changes in slope of said fluorescence intensity profile.

The present invention further discloses methods of measuring heat of crystallization, crystallinity and free volume cell size in a polymer by developing a plot of changes in fluorescence intensity versus temperature for a polymer doped with a fluorescent dye.

In preferred embodiments of the invention, DMA-DPH or BPP are utilized as the fluorescent dyes.

Other features and advantages of the invention will be set forth in, or apparent from, the detailed description of preferred embodiments of the invention which follows.

DESCRIPTION OF THE PREFERRED EMBODIMENTS

The present invention utilizes monomer and excimer producing dyes to detect the occurrence of thermodynamic phase transitions in polymers during injection molding. Injection molding machines operate in a cycle which consists of closing two mold halves under a clamping pressure, the injection of molten polymer resin into the mold cavity, the application of pressure to pack the resin in the mold, the release of resin packing pressure, a holding period during which the resin cools, release of the mold clamping pressure, and finally, the opening of the mold with simultaneous ejection of the polymer product. The mold is then closed again and the cycle is repeated. Opening the mold too soon will result in warping of the product shape, while allowing the product to remain in the mold too long results in decreased productivity. Accordingly, the present invention discloses a method which can be used to adjust the cycle so that holding pressure is applied and released, and the mold is opened at the optimum times.

Figure 1:
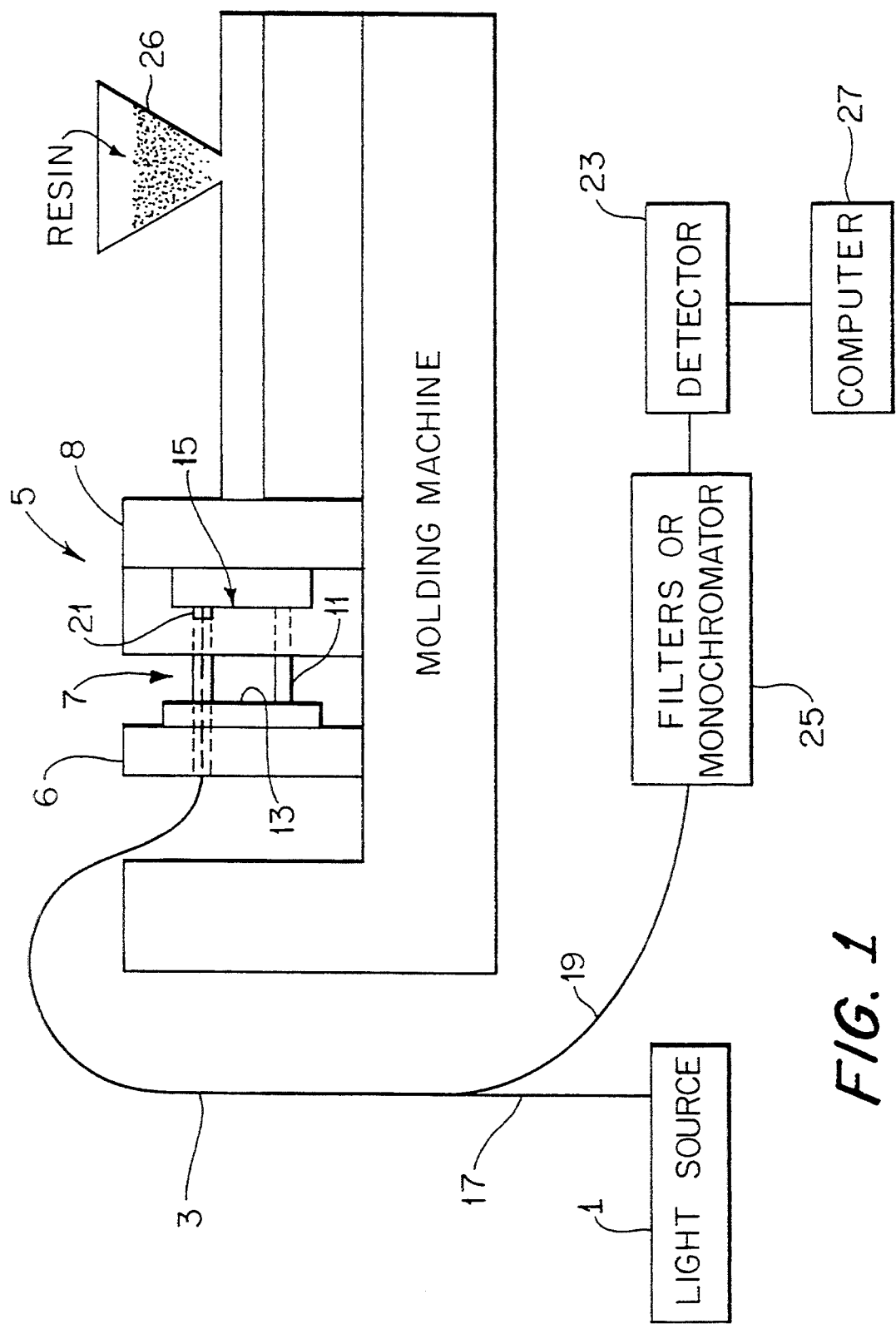
FIG. 1 shows a schematic of an optical measurement system incorporated with an injection molding machine.

Referring to the drawings and, more particularly, to FIG. 1, a diagram of a preferred embodiment of the optical measurement system used in the method of the present invention is shown. A xenon arc lamp serves as a light source 1 to excite the fluorescent dye. Alternatively, in another preferred embodiment, a laser source may be utilized. The excitation wavelength is separated from the full spectrum of the lamp using a grating monochromator or filter. Excitation light energy is transported via a bifurcated optical fiber cable 3 comprised of a bundle of fused silica fibers to the injection molding machine 5. The common end, or sensing tip of the optical fiber 3 is inserted into the mold using an ejector pin channel 7. A ruggedized optical fiber tip can serve as the ejector pin 11 itself in which case the sensing tip is held flush with the inside wall 13 of the mold cavity 15. Alternatively, the sensing tip can be inserted axially into an ejector pin sleeve which is fitted with an optical window 21 at its end. A first branch 17 of the optical fiber cable 3 carries the excitation light to the sensing tip and a second branch 19 collects fluorescence light from the excited dye near the sensing tip and transports it to the optical detector 23. The detector 23 consists of monochromators and/or filters 25 as are appropriate for the analysis of the fluorescence signal. In a preferred embodiment, photomultipliers are also utilized in conjunction with current amplifiers to detect the light intensity.

Dye may be added to the polymer using a number of different methods. For example, the dye may be put into a dilute solution and dripped into the resin hopper 26 on the molding machine 5. It can be pulverized and then mixed with the resin powder. Yet another method is to compound the dye with the melt resin using common polymer mixing equipment, as is done when adding color pigments. The dye can also be mixed with the polymer using a common solvent, and the solvent evaporated off.

During the injection molding process, measurements on the order of 100 per second are taken via the analog output of the current amplifiers, which is fed into a computer 27 via an analog to digital conversion board. Data taken during polymer solidification is then displayed as a curve of fluorescence intensity or the ratio of excimer to monomer fluorescence intensity ($I_{ex}/I_m$), hereinafter referred to collectively as "fluorescence intensity", vs time. Because the occurrence of solidification is detected by a change in slope of the fluorescence intensity vs. time curve, the absolute intensity of the fluorescence is not a factor. Also, the need to maintain uniform spatial distribution of the dye in the polymer resin is avoided. Using the change in slope of the curve and known behavior of the dye in the environment of the polymer, the point of solidification may be determined. Consequently, the mold may be opened at the optimum time in the mold cycle. For purposes of this invention, solidification is defined as the transition of phase from liquid to solid either by the formation of a glass or by crystallization.

In accordance with the method of the present invention, calibration curves providing a fluorescence vs. temperature characterization of the behavior of a dye in the environment of the host polymer are utilized for analysis of real-time measurements during injection molding. The application of fluorescence spectrometry to monitor polymer solidification during injection molding can employ any fluorescent dye which displays distinct spectral changes as the polymer solidifies. However, for experimental purposes, calibration curves were prepared by measuring fluorescence intensity and temperature during cooling of a molecular rotor dye (DMA-DPH) and an excimer producing dye (BPP) doped into a glass forming or amorphous polymer, polystyrene (PS), and a crystallizable polymer, polyethylene (PE). The polystyrene was PS 525P1 which is commercially available from Fina Corp. in pellet form, the polyethylene was Marlex TR885 in pellet form which is commercially available from Phillips Corp. Marlex TR885 contains an antioxidant which causes ultraviolet absorption in this material. The dyes are commercially available from Molecular Probes.

Each dye was mixed with the resins so that concentration of dye in the final molded product would be on the order of 10 ppm by weight, which is a sufficiently large concentration for producing detectable fluorescence. Different methods were used when adding the dye to PS and PE. For PS, a common solvent, toluene, was used to mix dye with the resin. An initial mixture of 30 grams of PS with 600 ppm dye was placed in solution. A thin film of polymer was prepared by spreading the solution onto a glass surface and permitting the solvent to evaporate. The film was then cut into small pieces which were dispersed with undoped PS resin pellets in a ratio that would average to 10 ppm by weight of dye in PS.

For PE, which is insoluble at room temperature, it was necessary to utilize pellets coated with the dye. This was accomplished by pouring a solution of dye onto polyethylene pellets and subsequently permitting the solvent to evaporate. The coated pellets were then dispersed with uncoated pellets so that the average dye concentration in the master batch was approximately 10 ppm by weight. Additional mixing of the dye occurred during the screw translation in the machine and during injection into the mold.

The procedure involved in preparing the calibration curves comprised placing approximately 10 grams of the doped resins in an oven with an optical fiber and thermocouple. The oven was first heated to 200° C. and then cooled to approximately 60° C. in 25 to 30 minutes. Cooling was not carried out as rapidly as it is during a typical injection molding process, but it was rapid enough to obtain the distinct characteristics of the fluorescence which marked the onset of solidification. BPP was excited at 345 nm and fluorescence was detected at 380 nm (monomer fluorescence) and over the wavelength regime between 450 to 550 nm (excimer fluorescence). For DMA-DPH, excitation was carried out at 400 nm and fluorescence emission was detected over a range of 470 to 530 nm.

FIGS. 2 through 5 show the resulting calibration curves of intensity (I) or excimer to monomer fluorescence intensity ratios ($I_{ex}/I_m$) vs. temperature. Changes in the fluorescence intensity reflect changes in molecular rotational relaxation time, the characteristic time which it takes a fluorescent molecule to rotate in its molecular environment.

Figure 2:
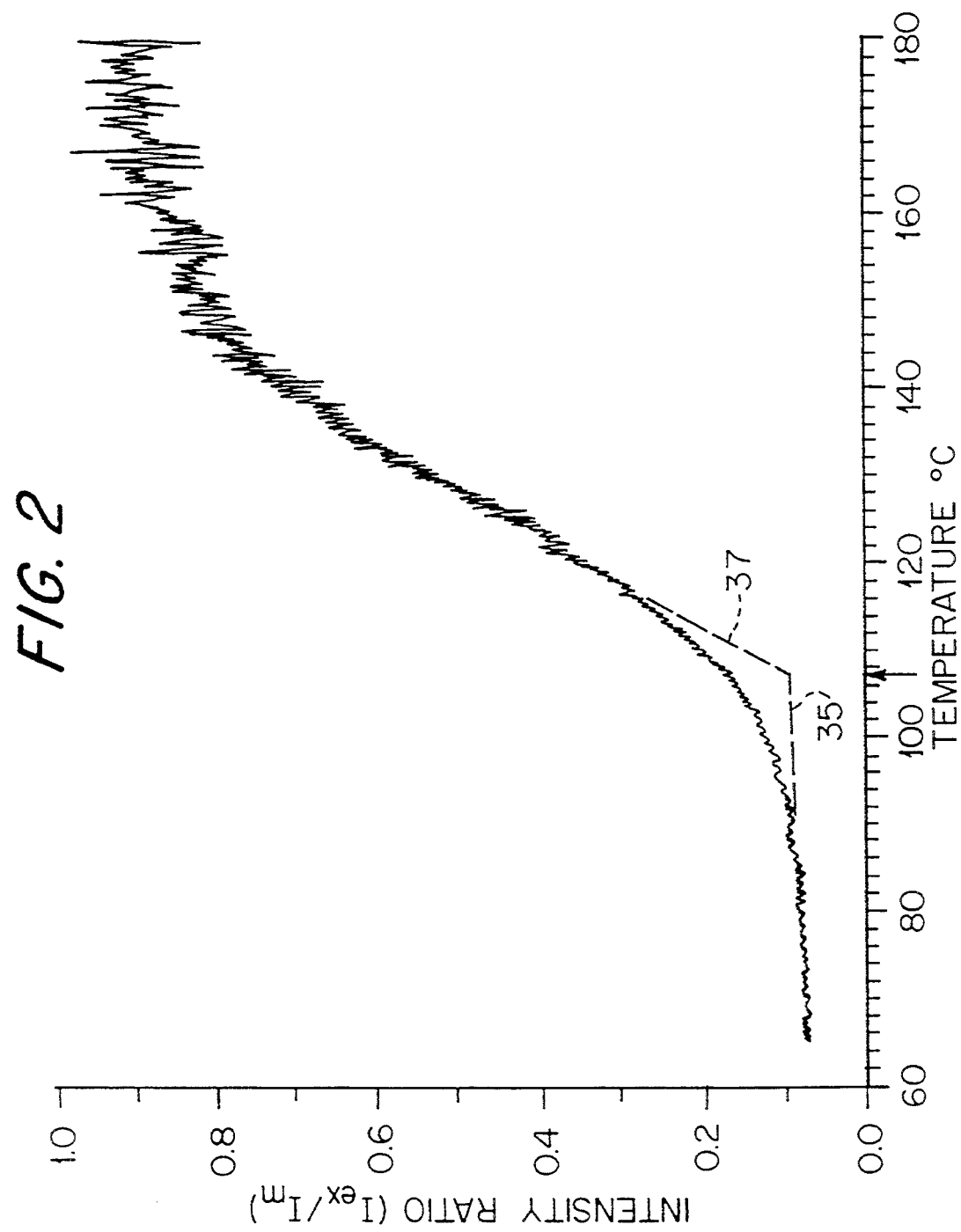
FIG. 2 shows a calibration curve of excimer to monomer fluorescence intensity ratio vs. temperature for polystyrene doped with BPP.

For BPP in polystyrene, which is shown in FIG. 2, the curve displays a knee at the liquid-to-glass transition. The glass transition temperature ($T_g$) for PS (approximately 105° C.) was defined as the intersection of two linear extrapolations 35, 37 of the curve from low and high temperatures, respectively. As temperature increased above $T_g$, the slope of the curve increased markedly. This is because the excimer intensity increased and the monomer intensity decreased upon raising the temperature above $T_g$. As the microviscosity of the resin decreased for $T>T_g$, the increased rotational freedom of the dye permitted the generation of more excimer fluorescence at the expense of the monomer fluorescence. Below $T_g$, the near zero slope in the curve indicates that PS is in the glassy state. This is due to restricted rotation of the large pyrene ring residing in free volume cells in the glass which are not large enough to accommodate this motion. Free volume cells are pockets of empty space, microscopic in size, which exist between molecules in a liquid or glass material. A range of free volume cell sizes is present in liquids with larger numbers of the small atomic size cells and relatively few of the molecule size of fifty or more atoms.

Figure 3:
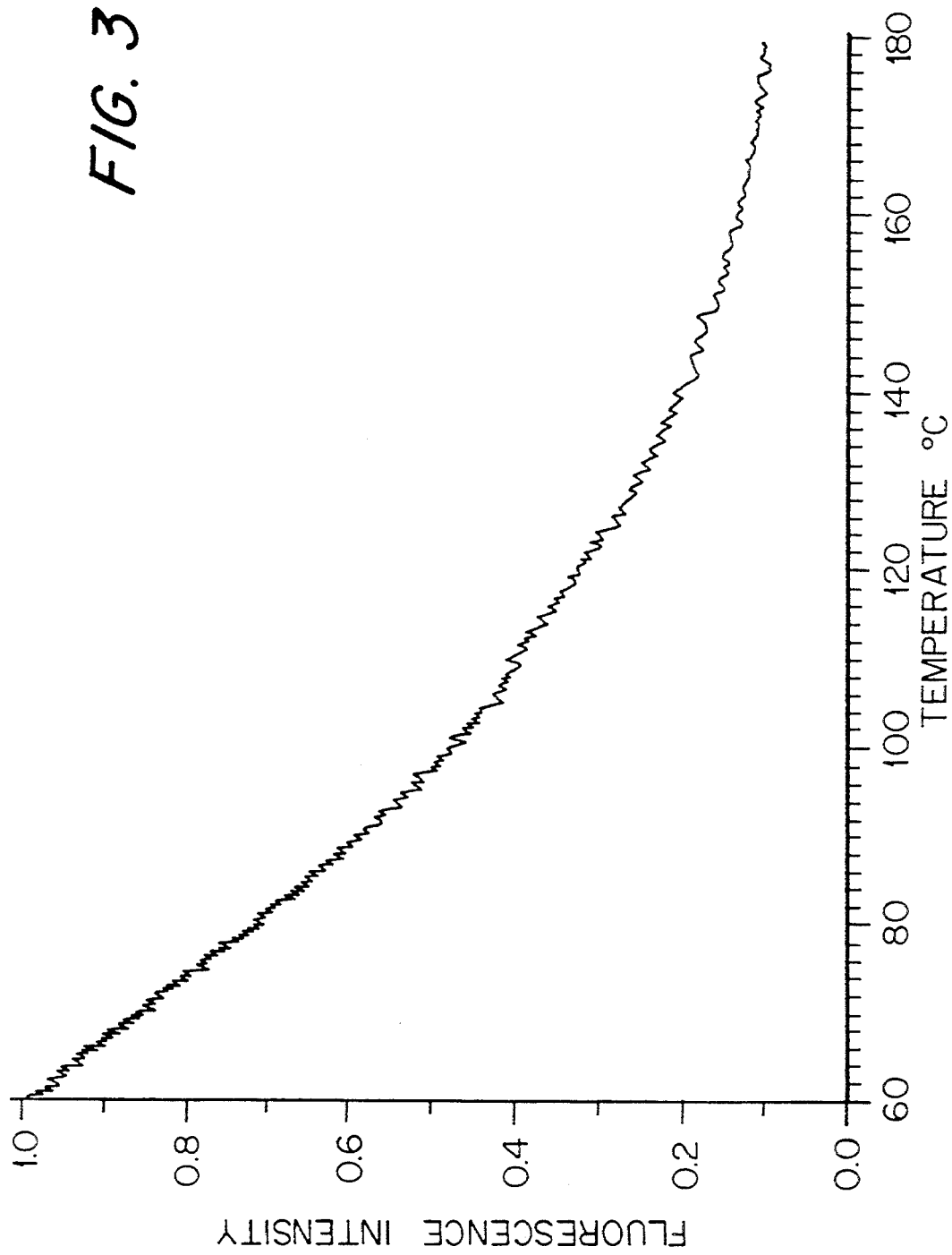
FIG. 3 shows a calibration curve of fluorescence intensity vs. temperature for polystyrene doped with DMA-DPH.

FIG. 3 shows the calibration curve for DMA-DPH in PS. DMA-DPH does not display the same sensitivity to the onset of the glass transition as does BPP even though both dyes respond to their molecular environment with similar functional dependence, that is, dependence on rotational relaxation time which in turn is proportional to $\eta/T$. The difference in their behavior below $T_g$ is attributed to $\eta$ which is peculiar to each molecule. DMA-DPH, whose end group requires much less free volume for rotational movement, is not as constricted by the glassy state as BPP. For BPP, the production of excimer requires a free volume of 0.43 nm$^3$ whereas DMA-DPH needs a relatively small $2.5\times10^{-2}$ nm$^3$ for the dimethyl amino end group rotation. Although BPP fluorescence is insensitive to changes in temperature below $T_g$, DMA-DPH changes significantly, and is advantageously employed in the injection molding experiments as a probe to monitor the changing temperature environment for $T<T_g$.

The data of FIGS. 2 and 3 highlight the influence of the dye molecule size relative to the size of free volume cells in PS, where free volume cells refer to volume throughout the polymer which is unoccupied by atoms or molecules. The free volume cells vary in size and are distributed throughout the polymer, the number of relatively small cells being greater than the number of large cells. As temperature approaches $T_g$ from above, free volume cell size decreases. Close to the $T_g$, shrinking free volume cell size causes inhibited molecular rotation of large dye molecules, but the motion of small molecules is unaffected. It is thus possible to measure the maximum volume of the distribution of free volume cell size in the glass by varying the size of the dye molecule and noting the smallest molecular size at which inhibited rotation occurs during the transition from liquid to glass phase, i.e. where a change in slope of the fluorescence intensity profile is still observed.

Figure 4:
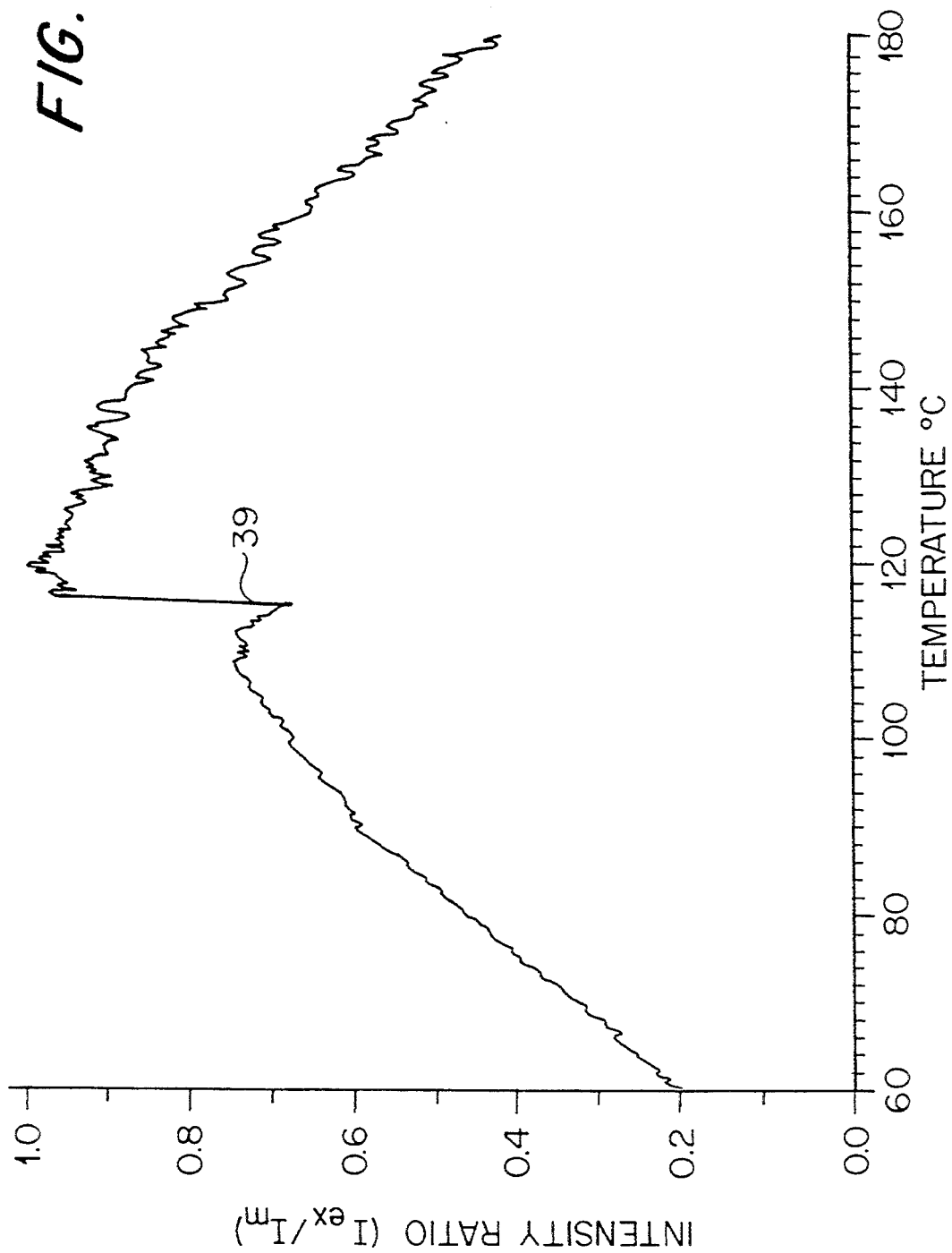
FIG. 4 shows a calibration curve of excimer to monomer fluorescence intensity ratio vs. temperature for polyethylene doped with BPP.

FIG. 4 shows the calibration curve for BPP doped into PE. The crystallization temperature $T_c$ is clearly indicated by the sharp discontinuity 39 in the curve at 117° C. The positive and negative slopes below and above $T_c$, respectively, originate from $T_c$, the two competing phenomena of intramolecular excimer formation and differences in optical transmission for the 380 nm monomer fluorescence and the 450–550 nm excimer fluorescence. In the melt, where $T>117°$ C., excitation light energy is transmitted deep into PE relative to transmission in crystalline PE which is limited due to light scattered by the microcrystals. For melt PE, the 380 nm fluorescence is disproportionately absorbed over the optical path within the bulk compared to absorption by the longer wavelength excimer fluorescence. This may be a result of the antioxidant or presence of carbonyl and hydroxyl groups in PE. By measuring the relative transmissions of 380 and 500 nm light in melt PE, it was confirmed that 380 nm light is absorbed to a greater degree than 500 nm light. It was further observed that the 380 nm absorption increases more rapidly with decreasing temperature than the 500 nm absorption due to the increase in 380 nm absorbance as density of melt PE increases. At $T_c$ (117° C.), a sharp drop in the excimer to monomer intensity ratio occurred as light scattering from the crystallites caused the excitation and detection of fluorescence to be concentrated at the surface. For $T<117°$ C., optical absorption for 380 nm and for the 450–550 nm range is comparable because the optical path is short and confined to the near surface.

Figure 5:
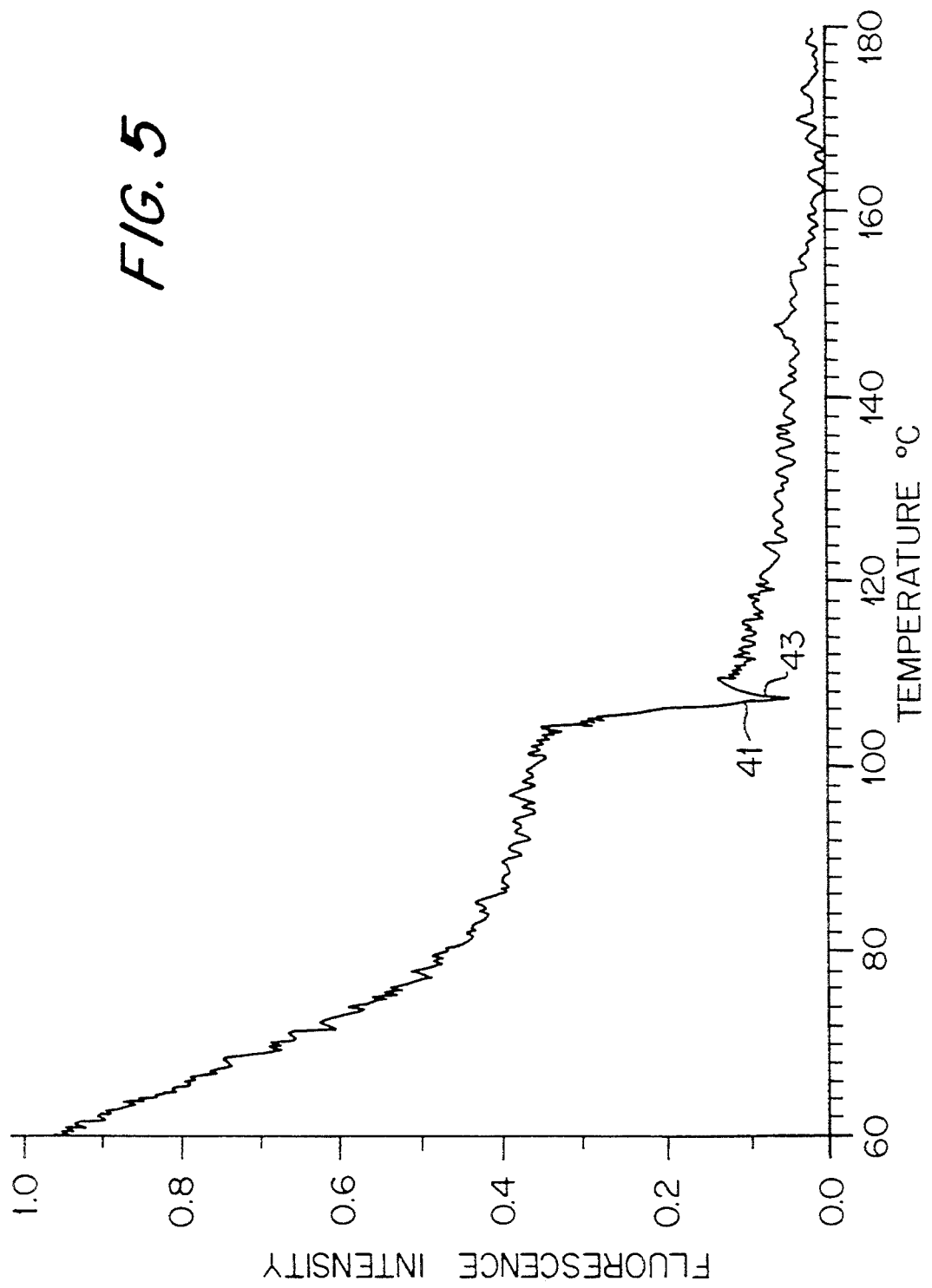
FIG. 5 shows a calibration curve of fluorescence intensity vs. temperature for polyethylene doped with DMA-DPH.

FIG. 5 shows the calibration curve for DMA-DPH in PE. The onset of crystallization of PE was observed at 109° C. where the fluorescence first decreased 43 and then increased 41 abruptly at 107° C. The decrease in fluorescence was due to the heat of crystallization which was released during the liquid-to-crystal transition. As PE crystallizes, the dye molecules, which are too large to be incorporated in the crystal, are displaced to the amorphous regions. As the heat of crystallization is conducted away from the crystallites, the dye experiences an increase in temperature with the result that $\tau_r$ of the DMA-DPH end-group decreases causing an increase in radiationless decay and a decrease in fluorescence. The abrupt increase 41 in fluorescence at 106°–107° C. upon crystallization was due to a combination of effects, including an increase in density of the material permitting more dye to come within the view of the optical sensor and the change in index of refraction which causes an increase in the background reflected light. Below $T_c$, the slope of the curve reflects the change in $\tau_r$ with temperature. The magnitude of the crystallization effect observed in this calibration curve is proportional to the cooling rate; the faster the cooling rate, the larger will be the production rate of heat energy from crystallization and the greater will be the momentary fluorescence response.

The above-described method can also be employed to measure changes in temperature of the polymer during heating and cooling conditions which effect a phase transition. To do this, a calibration curve of intensity or ratio of excimer to monomer fluorescence intensity versus temperature, such as the curves shown in FIGS. 2 through 5, is generated and a temperature scale is established by using the phase transition as a reference point. Knowledge of the phase transition temperature ($T_c$ or $T_g$) of the material under investigation in conjunction with the calibration curve fixes the fluorescence intensity temperature measurement scale. Temperature is measured by noting the change in fluorescence intensity with respect to the intensity at the reference temperature. In this manner, temperature measurements are made without the need for absolute measurement of fluorescence intensity.

Further, the method can be used to measure the crystallinity and the heat of crystallization of a polymer which evolves during the liquid to crystal transition. For these measurements, the vessel containing the doped resin is converted to a calorimeter, i.e. an insulated chamber with known specific heat. Using a calibration curve, such as the one shown in FIG. 5, the change in temperature accompanying the phase transition can be obtained from the observed change in fluorescence intensity as described above. From knowledge of the specific heat and mass of the polymer and specimen vessel, a heat of crystallization can be obtained following equation:

$$\Delta H = C_{ps} m_s \Delta T + C_{pv} m_v \Delta T,$$

where $C_{ps}$ is the specific heat of the polymer specimen, $m_s$ is the mass of the polymer specimen, $C_{pv}$ is the specific heat of the specimen vessel, $m_v$ is the mass of the vessel, and $\Delta T$ is the change in temperature of the specimen and vessel at crystallization. In addition, if the heat of fusion of the polymer is known, then the crystallinity $\chi$ can be calculated from the equation:

$$\chi = \Delta H / \Delta H_{100} = \Delta H / m_s H_f,$$

where $\Delta H_{100}$ is the heat of crystallization if 100% of the polymer specimen crystallizes and $H_f$ is the heat of fusion for the specimen.

After obtaining the calibration curves of FIGS. 2–5, insitu, real-time measurements of fluorescence intensity during injection molding for BPP and DMA-DPH in PS and PE were obtained, the results of which are shown in FIGS. 6–9. Fluorescence intensity and pressure levels are detected for various time intervals and then plotted versus time during the injection mold cycle. The time scales of the two sets of data are coincident within 0.5 seconds and it was assumed that cooling rates were the same. The pressure levels indicate the clamping pressure used to lock the mold halves together and pressures exerted by the hydraulic ram on the polymer as it is injected into the mold and held in the cavity during the cooling period. The changes in the pressure data serve as event markers in the mold cycle.

The experimental procedure utilized for the data of FIGS. 6 and 7 was as follows: the mold was closed with the application of clamping pressure (147 MPa) at $t \approx 5$ seconds; polymer fill pressure (31 MPa) was applied at 7 seconds and fill was complete at approximately 9 seconds; as the polymer cooled, hold pressure was applied to the polymer from 9 to 39 seconds; hold pressure was released at 39 seconds and the polymer cooled further under zero applied pressure. In normal operation, releasing the packing pressure and opening the mold would occur sooner; however, for purposes of experimentation, the mold remained closed while data was obtained over a time period in excess of the optimum mold time.

Figure 6:
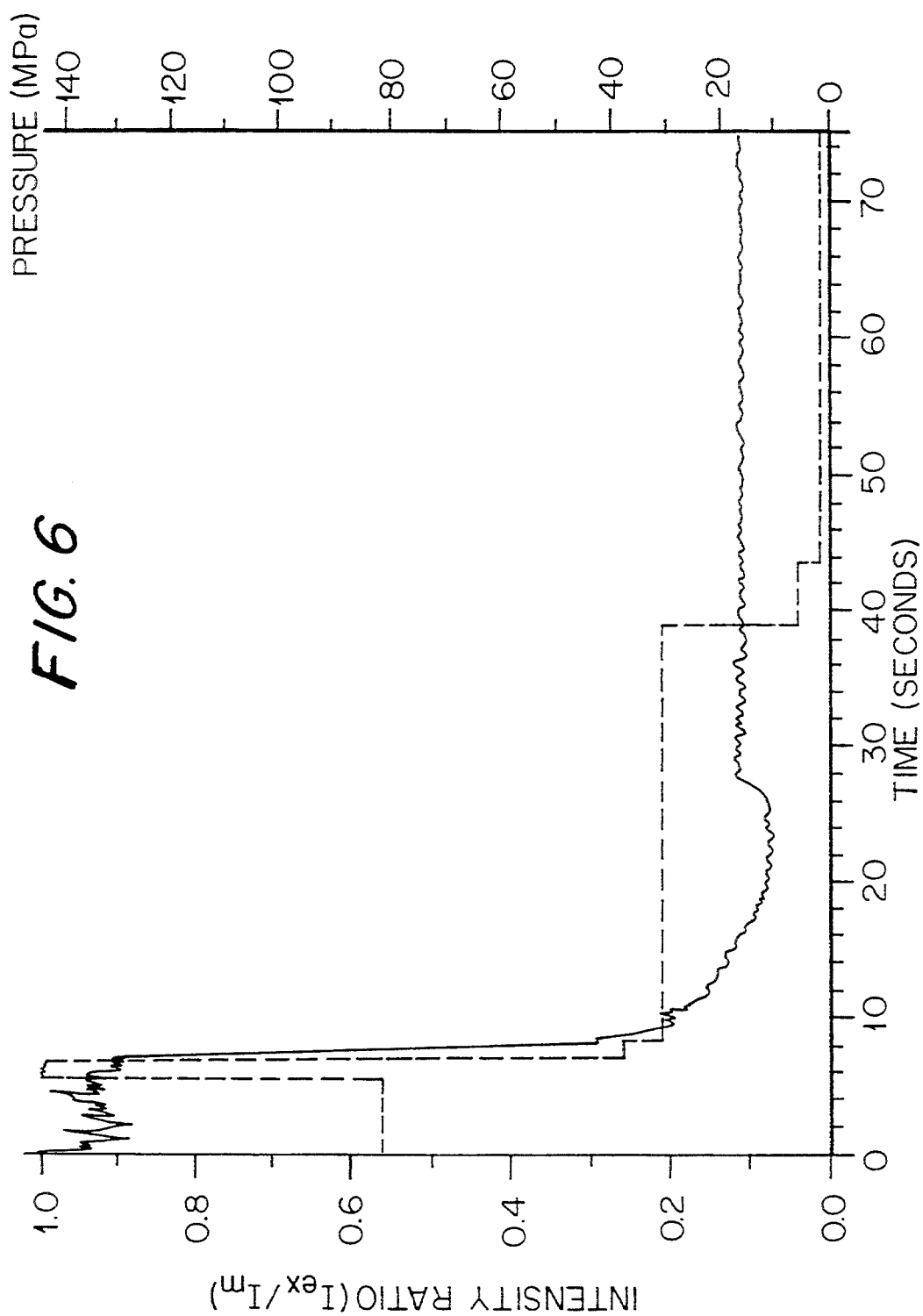
FIG. 6 shows a plot of pressure and excimer to monomer fluorescence intensity ratio vs. time during injection molding for BPP doped into polystyrene.
Figure 7:
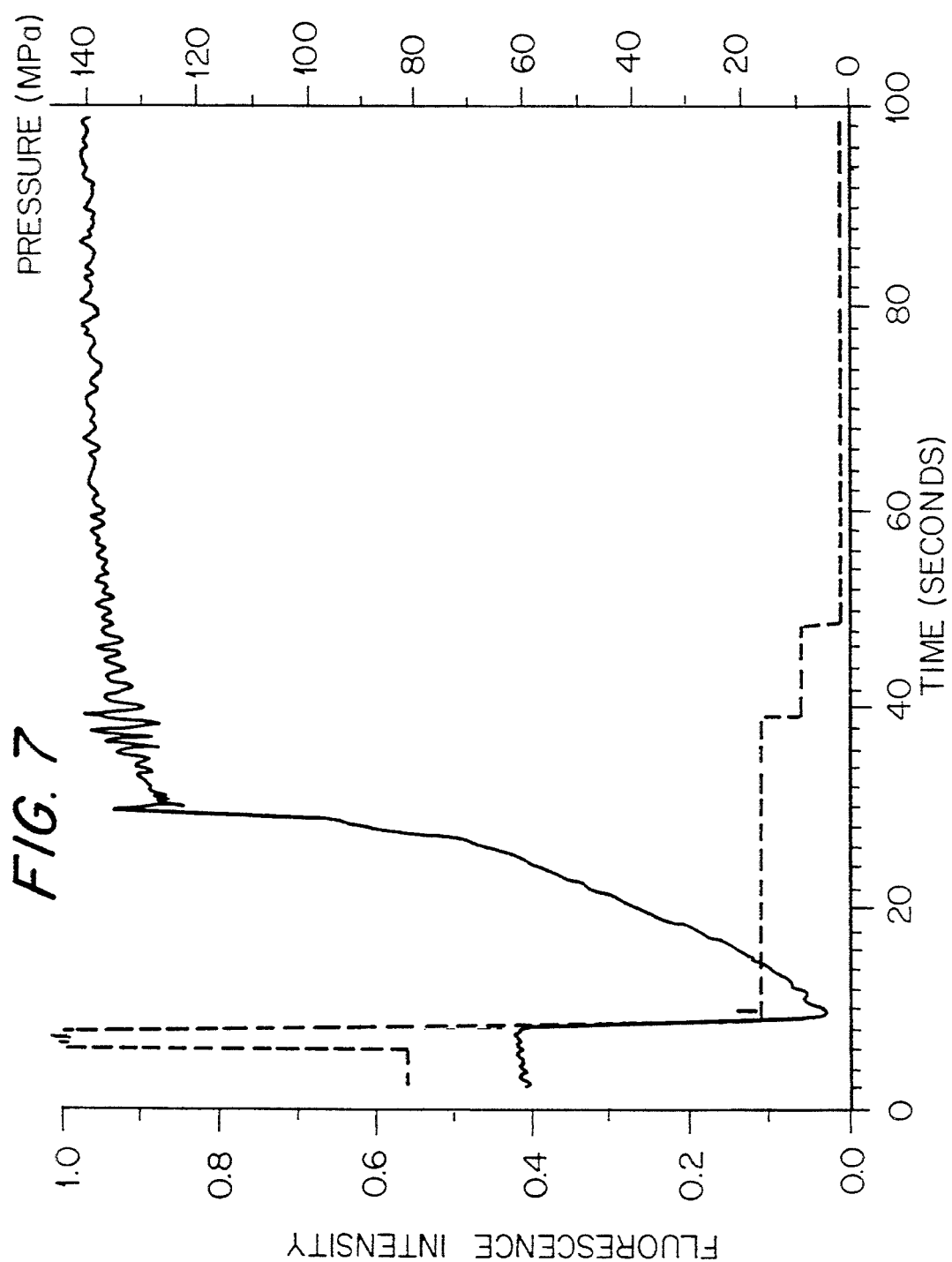
FIG. 7 shows a plot of pressure and fluorescence intensity vs. time during injection molding for DMA-DPH doped into polystyrene.

FIGS. 6 and 7 show $I_{ex}/I_m$ versus time for BPP in PS and I versus time for DMA-DPH in PS. The signal obtained initially represents an empty mold, where the signal is simply background from the excitation light which reflects off the wall of the mold and back into the collection fibers. As the mold filled over a time period of about 7 to 9 seconds, this background decreased and the characteristic signal from the fluorescent dye was observed. At $t=20$ seconds, the slope of the curve in FIG. 6 became approximately zero as the polystyrene cooled below $T_g$. The slight increase at 27 seconds may be interpreted as an optical effect which occurred when the specimen pulled away from the sensor as it cooled and the reflection of light from the sapphire window/polystyrene interface changed. The slope of the curve remained zero after release of the packing pressure indicating that the polystyrene remained in the glassy state.

The constant level of fluorescence in the data of FIG. 6 for $t > 20$ seconds is due to highly restricted excimer production below $T_g$ of the PS. The fact that the temperature was still decreasing for $t > 20$ seconds ($T < T_g$) is seen from the real-time fluorescence for DMA-DPH in PS shown in FIG. 7. As with the calibration experiment, a distinct change in the DMA-DPH fluorescence signal indicating the onset of the glass transition was not observed. According to the BPP data of FIG. 6, the liquid-to-glass transition occurred at approximately 20 seconds and, as expected, there is no indication of this transition in the DMA-DPH data of FIG. 7. Instead, it was observed that the DMA-DPH fluorescence continued to change monotonically at t=20 seconds indicating that the temperature of PS continued to decrease. At t=27 seconds, separation of specimen from the sapphire window produced a discontinuous change in reflection at the sapphire/air/specimen interface. The DMA-DPH fluorescence began to plateau at approximately 55 seconds and the slow change thereafter was a reflection of the asymptotic approach of the PS temperature to the ambient temperature of the mold.

Figure 8:
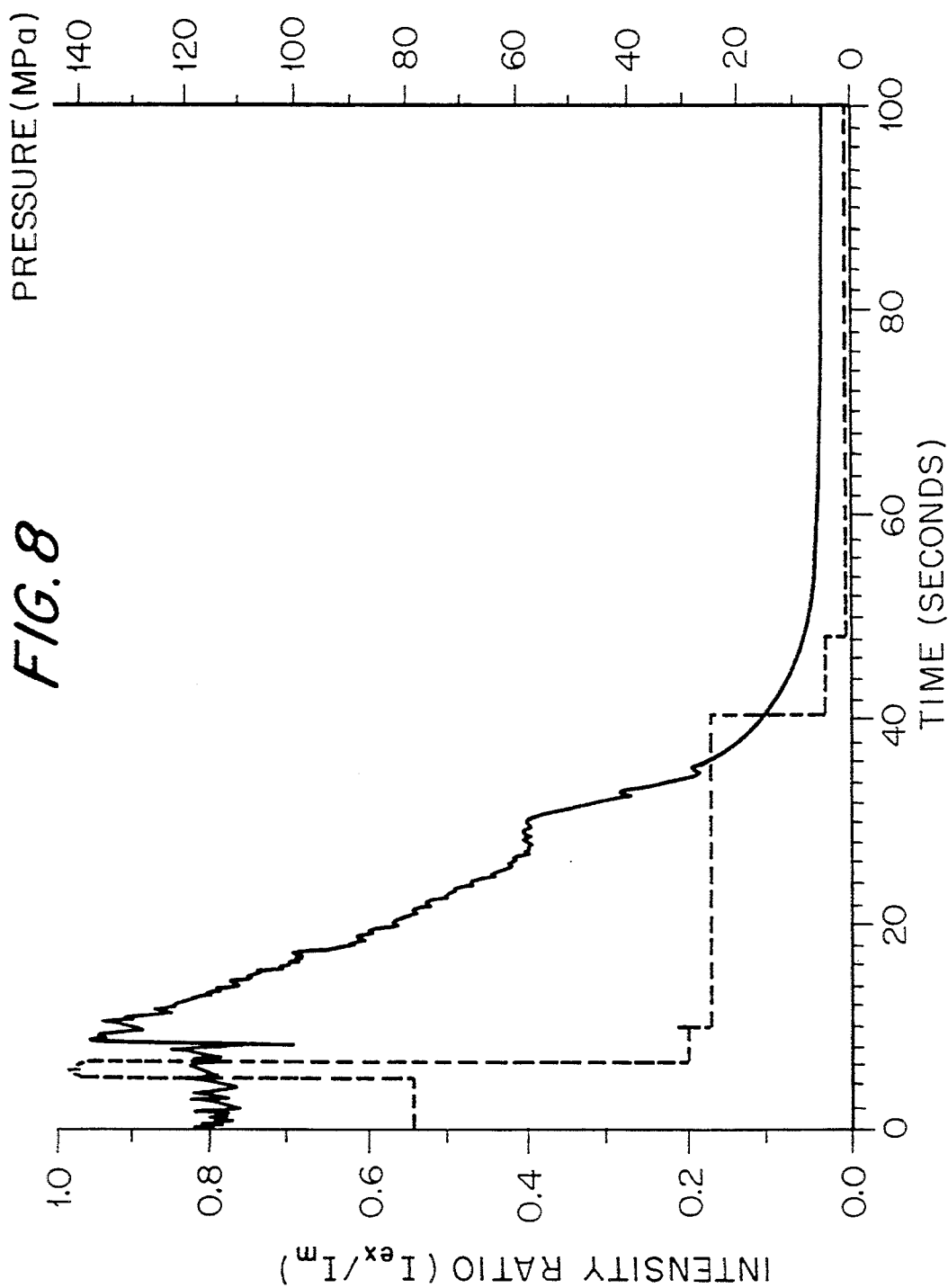
FIG. 8 shows a plot of pressure and excimer to monomer fluorescence intensity ratio vs. time during injection molding for BPP doped into polyethylene.
Figure 9:
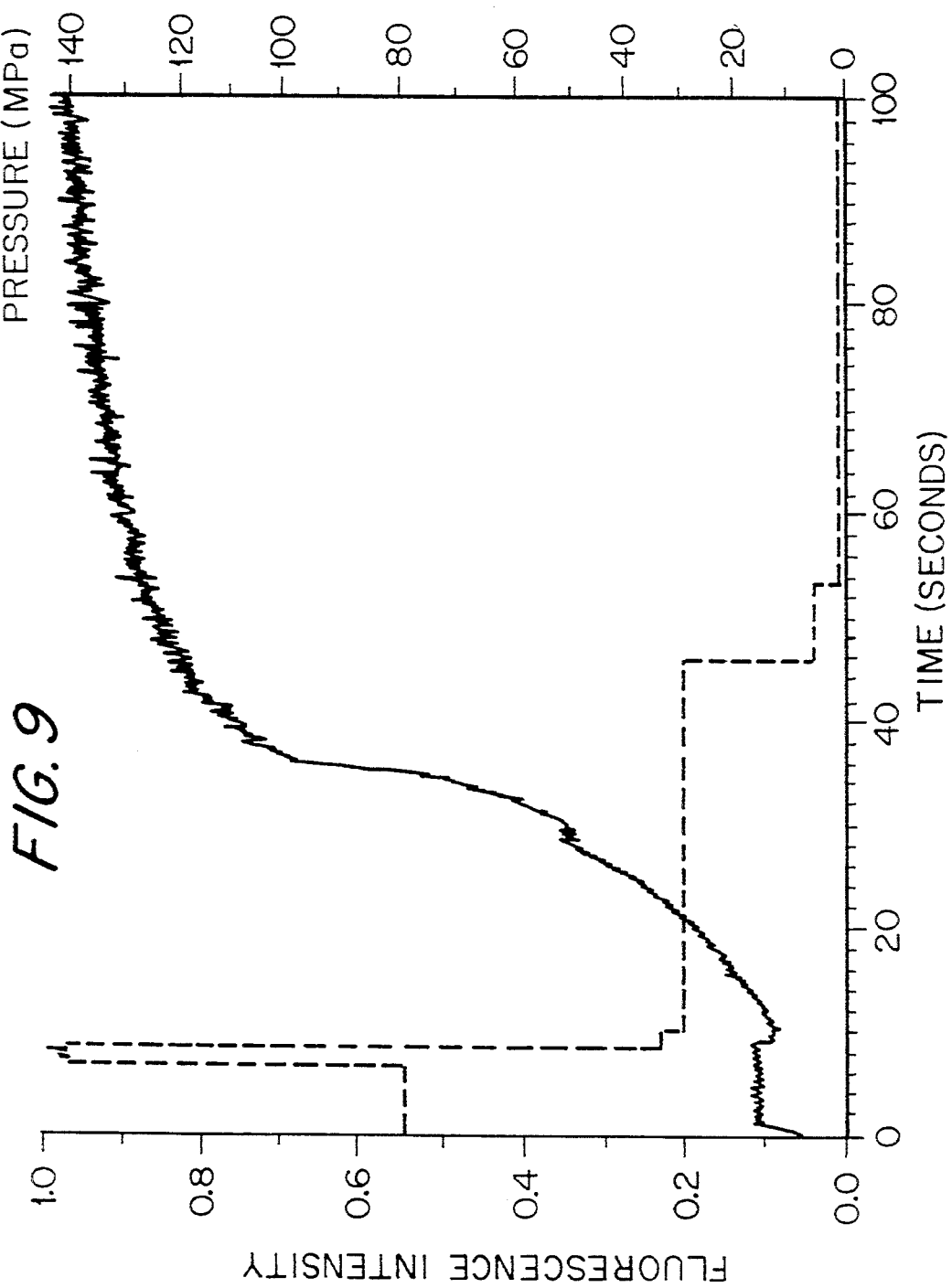
FIG. 9 shows a plot of pressure and fluorescence intensity vs. time during injection molding for DMA-DPH doped into polyethylene.

FIGS. 8 and 9 show the real-time fluorescence intensity and pressure data for BPP and DMA-DPH in PE. After the mold fill was complete at t≈6 seconds, it was observed that fluorescence displayed uneventful change until crystallization occurred at t≈27 seconds. The release of the heat of crystallization transpired over a time period of 27 to 30 seconds after which the curves showed monotonic changes due to cooling. For t>30 seconds some of the fluorescence intensity changes were caused by the increase in density accompanying crystallization and scattering of light in the crystallized PE. The abrupt increase which occurred at 36 seconds in the DMA-DPH curve (FIG. 9), may be interpreted as a change in optical reflection at the sapphire/specimen interface which accompanied the separation of the specimen from the sensor upon shrinkage. For both curves, the fluorescence intensity approached a plateau for long times as the temperature of PE approached the ambient mold temperature.

Comparison of FIG. 8 with the FIG. 4 calibration curve for BPP/PE indicates that there was no time region during the injection mold cycle for which ultraviolet absorption effects were observed. This indicates that a crystalline skin forms almost immediately at the surface of the mold and that the observations are from the near surface. Since the temperature of the mold was held near 23° C. by circulating water coolant, rapid crystallization occurred. From 10 seconds to 100 seconds, $I_{ex}/I_m$ decreased monotonically except for changes at 27 seconds (crystallization) and 36 seconds (specimen/sensor separation). The major differences in the experiments generating the two curves (FIGS. 4 and 8) were the time scale and the magnitude of the temperature gradients.

It will be evident to those skilled in the art that the invention is not limited to the details of the foregoing illustrative embodiments and that the present invention may be embodied in other specific forms without departing from the specified or essential attributes thereof. The present embodiments are therefore to be considered in all aspects as illustrative and not restrictive, the scope of the invention being indicated by the appended claims rather than by the foregoing description, and all changes which come within the meaning and range of equivalencies of the claims are therefore intended to be embraced therein.

We claim:

1. A method of detecting thermodynamic phase transitions in a polymer during injection molding comprising the steps of:
    selecting a polymer for injection molding;
    selecting a fluorescent dye to detect thermodynamic phase transitions in said polymer based on a desired temperature response or a desired molecular size;
    mixing said fluorescent dye with said polymer;
    injecting said fluorescent dye and said polymer into a mold; exciting said fluorescent dye with a light source;
    adjusting temperature of said polymer to effect a phase transition in said polymer;
    detecting changes in fluorescence intensity in said fluorescent dye caused by heat of crystallization or collapse of free volume cell size at various time intervals during said step of adjusting;
    developing a fluorescence intensity profile by plotting said changes in fluorescence intensity versus time; and
    determining phase transitions in said polymer from changes in slope of said fluorescence intensity profile.

2. The method according to claim 1 wherein said polymer is a crystallizing polymer.

3. The method according to claim 1 wherein said polymer is an amorphous polymer.

4. The method according to claim 2 wherein said polymer is polyethylene.

5. The method according to claim 3 wherein said polymer is polystyrene.

6. The method according to claim 1 wherein said dye is 1-(4-dimethylaminophenyl)-6-phenyl-1,3,5 hexatriene.

7. The method according to claim 1 wherein said dye is bis(pyrene) propane.

8. The method according to claim 7 wherein said step of detecting comprises measuring excimer and monomer fluorescence and said fluorescence intensity comprises a ratio of said excimer to monomer fluorescence.

9. The method according to claim 1 wherein said light source is a xenon arc lamp.

10. The method according to claim 1 wherein said light source is a laser.

11. The method according to claim 1 wherein fluorescence changes are detected by monochromators or filters.

* * * * *